United States Patent [19]

McArthur et al.

[11] Patent Number: 4,874,372
[45] Date of Patent: Oct. 17, 1989

[54] NON-REUSABLE SYRINGE

[76] Inventors: William McArthur, 23041 LaGranja Dr., Valencia, Calif. 91354; Thomas M. Soukup, 4722 Karling Pl., Palmdale, Calif. 93550

[21] Appl. No.: 251,201

[22] Filed: Sep. 27, 1988

[51] Int. Cl.⁴ .............................................. A61M 5/00
[52] U.S. Cl. ................................... 604/110; 604/218; 604/228
[58] Field of Search ................ 604/110, 218, 228, 187

[56] References Cited
U.S. PATENT DOCUMENTS 4,775,363  10/1988  Sandsdalen .......................... 604/110
4,775,364  10/1988  Alles .................................... 604/110

Primary Examiner—John D. Yasko
Attorney, Agent, or Firm—James E. Brunton

[57] ABSTRACT

A syringe which can be used only once. The syringe includes a body having a fluid chamber, a plunger reciprocally movable within the chamber and a handle for moving the plunger within the chamber. Following the injection cycle, the handle automatically disconnects from the plunger rendering the device useless.

13 Claims, 1 Drawing Sheet

NON-REUSABLE SYRINGE

BACKGROUND OF THE INVENTION

1. Field of the Invention

The present invention relates generally to syringes. More particularly, the invention concerns a non-reusable syringe and needle of the character used to inject fluids into the body.

2. Discussion of the Prior Art

In recent times there has been an alarming increase in the spread of infectious diseases such as AIDS and hepatitis among drug users who reuse or share injection needles or syringes. The thrust of the present invention is to provide a syringe of novel design which can be used only once to inject fluids into the body.

In one form of the apparatus of the present invention, the handle which moves the plunger of the syringe from a first position to a second retracted position to draw fluid into the syringe from an external source is interconnected with the plunger by a special material which dissolves upon being exposed to fluid. The syringe can be actuated in air as many times as desired, but once filled with fluid and a pressure applied to depress the plunger to eject the fluid from the chamber through a needle, fluid enters a passageway in the plunger which exposes the special connector material to the fluid causing it to lose its structural integrity. If a refill of the syringe is attempted the handle simply pulls away from the plunger leaving the plunger in its depressed position. With the handle thus disconnected from the plunger, the syringe becomes useless since fluid from an external source cannot be drawn into the chamber for subsequent injection into the body. As will be discussed in greater detail hereinafter, the connecting medium or soluble material used to initially interconnect the handle and the plunger of the apparatus can be any type of biocompatible material which has structural integrity when dry, but which loses its structural integrity when exposed to a liquid.

SUMMARY OF THE INVENTION

It is an object of the present invention to provide a syringe of the character used to inject fluids into the body which can be used but a single time to draw fluid into the chamber of the syringe from an external source and then to eject the fluid from the syringe.

It is another object of the invention to provide a syringe of the aforementioned character in which the plunger of the syringe and the actuating handle thereof are interconnected by a connector material which has structural integrity when dry, but which loses structural integrity when exposed to a fluid. The plunger of the apparatus is specially designed to include an internal bore which receives one end of the handle and also contains the connector material. A fluid passageway leads to the internal bore so that upon downward movement of the plunger to eject the fluid from the syringe, a portion of the fluid will flow through the passageway into the internal bore causing the connector material to lose its structural integrity.

It is another object of the invention to provide a syringe of the character described in the preceding paragraph in which a number of different biocompatible materials can be used as the connector material to interconnect the handle and the plunger.

It is still another object of the invention to provide a syringe of the character described which is of highly simple construction, is easy to use, and can be inexpensively manufactured in large quantities.

DESCRIPTION OF THE INVENTION

Figure 1:
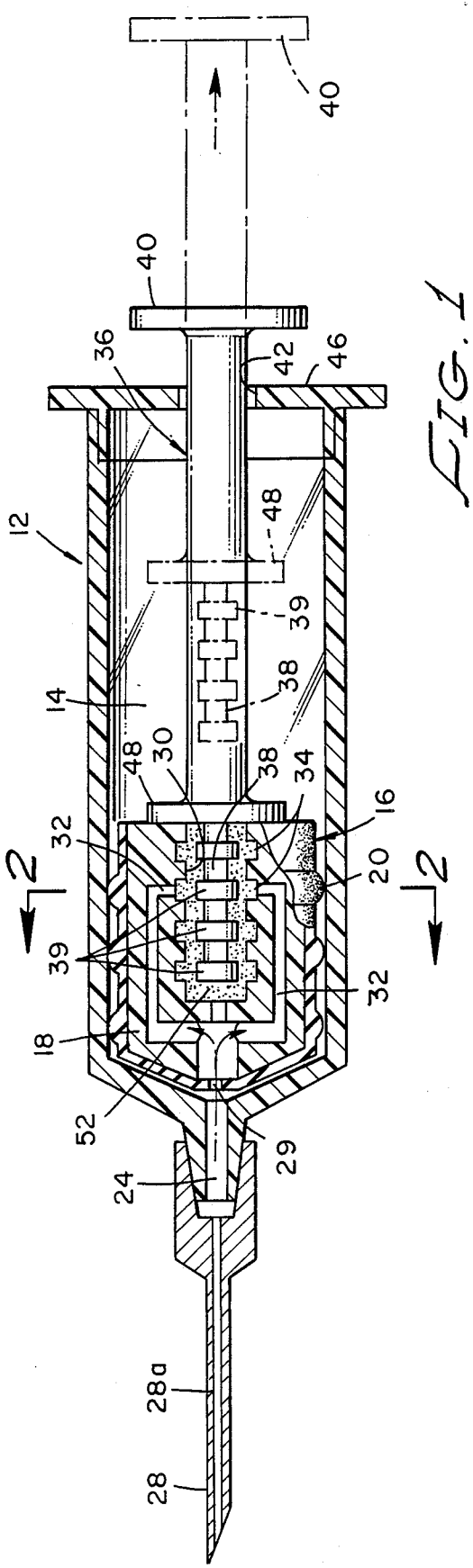
FIG. 1 is a longitudinal sectional view of the syringe in accordance with the present invention.
Figure 2:
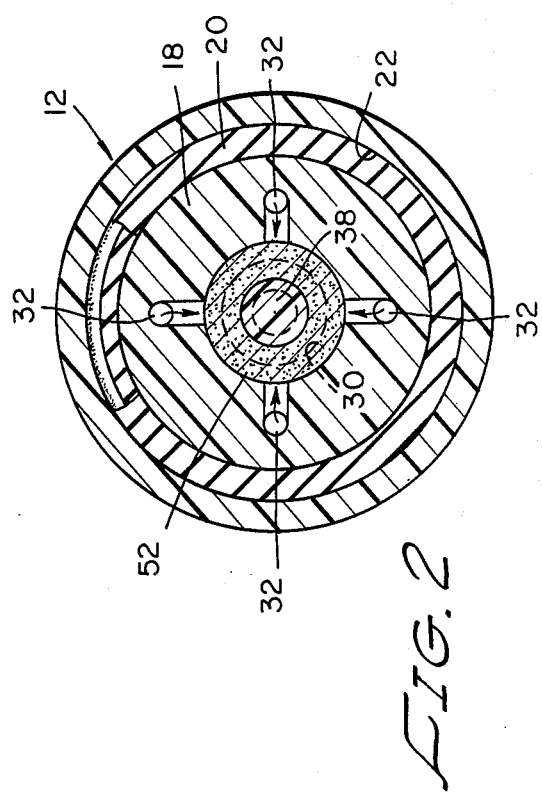
FIG. 2 is and elongated sectional view of the syringe taken along the line 2—2 of FIG. 1.

Referring to the drawings, the reusable syringe of the present invention comprises a hollow cylindrical body 12 having an internal chamber 14 within which a plunger means generally designated by the numeral 16, is reciprocally movable. In the present embodiment of the invention, the plunger means is provided in the form of a plunger 18 which is surrounded by an elastomeric material 20 which sealably engages the inner wall 22 of syringe body 12.

Body 12 is provided with a fluid inlet 24 which is in communication with the internal chamber of the body. An injection needle 28 of standard construction is interconnected with body 12 proximate fluid inlet 24 so that the fluid inlet 24 is in communication with the internal bore 28a of the needle 28.

The plunger body 18 is provided with a counter-bore, or internal chamber, 30 and fluid passageways 32 which interconnect the internal chamber with the fluid inlet 24 via a fluid opening 29 provided in the elastomeric covering 20. Internal chamber 30 is provided with at least one enlarged diameter circumferential groove 34 the purpose of which will presently be described.

Forming an important aspect of the apparatus of the present invention is handle means, here provided in the form of an elongated handle 36, having a forward stem portion 38 and a rearward finger engaging portion 40 which extends outwardly from body 12 through an opening 42 formed in the end closure wall 46 of the syringe body 12. Stem portion 38 is provided with gripping means, here comprising at least one enlarged diameter portion 39, the purpose of which will presently be described.

A unique connector means is provided for releasably interconnecting the plunger handle with the plunger means so as to permit only one movement of the plunger from the first position shown in FIG. 1 to the second retracted position shown by the phantom lines in FIG. 1. Stated another way, the connector means of the invention performs the very important function of rigidly interconnecting the handle and the plunger so as to permit the retraction of the plunger to draw fluid from an external source through needle 28 and inlet passageway 24 into internal chamber 14 of the syringe body. However, following the retraction of the plunger and a subsequent return of the plunger to its starting position to eject the fluid, the handle and the plunger will become automatically disconnected thereby preventing a second retraction of the plunger from the first position to the second position.

In the embodiment of the invention shown in the drawings the connector means comprises a connecting medium, or material, 52 which is disposed within internal chamber or counter-bore 30. Material 52 surrounds the stem portion 38 and the gripping means of the stem portion 38 of the plunger handle in a manner such as to rigidly interconnect the plunger handle with the plunger body 18. More particularly, the connector material surrounds the enlarged diameter rings provided on the stem and also fills the enlarged diameter grooves 34 provided within the internal chamber 30. With this construction the connector material 52, when in a dry form securely bonds the stem 38 of the handle to the plunger body 18.

Connector material, or medium, 52 may be any type of material which is solid and has mechanical integrity when dry, but which loses mechanical integrity when exposed to a fluid. The material may be a simple inexpensive material such as sugar or it may be a biocompatible hydrolyzable polymeric material such as an absorbable suture material or any material that loses strength within a short time after exposure to a liquid.

It is to be understood that the connector means can also take the form of a mechanical disconnection mechanism, such as a latch, which functions to disconnect the handle from the plunger after a first retraction. Similarly, the connector means can take the form of a differential friction device, a quick release threaded interconnection or a variety of other disconnect mechanisms well known to those skilled in the art.

OPERATION

With the stem 38 of the handle rigidly bonded together with the plunger body 18 by a suitable connector material 52, a rearward force exerted on portion 40 of the handle will cause the plunger means to be sealably retracted within chamber 14 of the syringe from the at rest first position to the second retracted position. This will cause fluid to be drawn from an external source through needle 28 through inlet passageway 24 and into the internal chamber of the syringe. A subsequent forward pressure exerted on handle portion 40 will cause a flange 48 of the handle member to engage the rear surface of the plunger body 18 urging the plunger forwardly of the syringe body within chamber 14 to its first, starting position. As the plunger means moves forwardly, a portion of the fluid contained within the chamber will pass through fluid opening 29 provided in the elastomeric covering and will flow through passageways 32 formed in the plunger body toward internal chamber or counter-bore 30. As soon as this fluid reaches the internal chamber the connector material 52 will start to dissolve and begin to lose its structural integrity. As the fluid continues to be forced into internal chamber 30 by the forward movement of the piston, a sufficient amount of the material 52 will be dissolved, or otherwise be exposed to the fluid, so as to lose structural integrity. Any second attempt to pull the plunger body rearwardly of the syringe will then cause the stem portion of the handle to pull free from the plunger, thereby preventing a second retraction of the plunger within the syringe. This structural disconnection of the plunger handle from the plunger renders the syringe useless thereby preventing any reuse of the syringe for a subsequent injection by the initial user or by any other user.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. Non-reusable syringe for drawing fluid from a fluid source comprising:
   (a) a body having a fluid chamber and a fluid inlet in communication with said fluid chamber;
   (b) plunger means reciprocally movable within said fluid chamber from a first position to a second position to draw fluid from the fluid source through said fluid inlet toward said fluid chamber, said plunger means comprising a plunger sealably movable within said fluid chamber, said plunger having an internal chamber and a fluid passageway interconnecting said internal chamber with said fluid inlet of said body;
   (c) a plunger handle for moving said plunger between said first and second positions; and
   (d) connector means for interconnecting said plunger handle and said plunger means for permitting only one time movement of said plunger means from said first position to said second position.

2. A non-reusable syringe as defined in claim 1 in which said plunger handle includes a stem receivable within said internal chamber of said plunger and in which said connector means comprises a hydrolyzable medium contained within said internal chamber for interconnecting said stem and said plunger.

3. A non-reusable syringe as defined in claim 2 in which said medium comprises a material having structural integrity when dry but losing structural integrity upon being exposed to the field from the fluid source.

4. A non-reusable syringe as defined in claim 3 in which said medium comprises sugar.

5. A non-reusable syringe as defined in claim 3 in which said medium comprises a biocompatible hydrolyzable polymeric material.

6. A syringe apparatus for drawing fluid from a fluid source comprising;
   (a) a body having a fluid chamber and a fluid inlet in communication with said fluid chamber;
   (b) plunger means reciprocally movable within said fluid chamber from a first position to a second position to draw fluid from the fluid source through said fluid inlet toward said fluid chamber;
   (c) handle means for moving said plunger between said first and second position said handle means including means for moving said plunger means from said second position to said first position to cause said material to be exposed to fluid; and
   (d) connector means for releasably interconnecting said handle means and said plunger means to permit movement of said plunger means from said first position to said second position and then from disconnecting said handle means from said plunger means to prevent subsequent movement from said plunger means from said first position to said second position, said connector means comprising a material which loses structural integrity upon exposure to fluid.

7. A syringe apparatus as defined in claim 6 in which said connector means comprises a material which loses structural integrity upon exposure to fluid and in which said handle means includes means for moving said plunger means from said second position to said first position to cause said material to be exposed to fluid.

8. A syringe apparatus as defined in claim 7 in which said connector means comprises a biocompatible liquid soluble material.

9. A syringe and needle of the character used to inject fluid into the body comprising;

(a) a chamber for containing fluid, said chamber having a fluid inlet in communication with the needle;
(b) a plunger sealably movable within said chamber from a first position to a second position to draw fluid from an external source through said fluid inlet into said chamber, said plunger having a counter-bore and a fluid passageway providing a fluid flow path between said fluid inlet of said chamber and said counter-bore whereby upon movement of said plunger from said second position to said first position fluid will be caused to flow through said fluid passageway into said counter-bore;
(c) An elongated handle having a first portion extending from said chamber and a second portion extending into said counter-bore of said plunger; and
(d) a connecting medium contained within said counter-bore of said plunger for releasably connecting said second portion of said handle to said plunger prior to exposure of said connecting medium to fluid, said connecting medium, comprising a material having structural integrity when dry and losing structural integrity when exposed to a fluid whereby upon movement of said plunger from said second position to said first position said connector medium will be exposed to fluid flowing through said passageway toward said internal chamber so that said connector medium will lose structural integrity thereby preventing subsequent movement of said plunger from said first position to said second position.

10. A syringe and needle as defined in claim 9 in which said second portion of said handle comprises a stem having gripping means for gripping said connector medium.

11. A syringe and needle as defined in claim 9 in which said plunger includes a yieldably deformable sealing material for sealably engaging said chamber.

12. A syringe and needle as defined in claim 9 in which said handle comprises a third portion disposed intermediate said first and second portions for engagement with said plunger to move said plunger from said second position to said first position.

13. A syringe and needle as defined in claim 9 in which said connector medium comprises a biocompatible hydrolyzable polymeric material.

* * * * *